United States Patent [19]
Klobucar et al.

[11] Patent Number: 6,019,940
[45] Date of Patent: Feb. 1, 2000

[54] METHOD OF PROCESSING INDUSTRIAL AIR STREAM FOR MEDICAL STERILIZERS

[75] Inventors: Joseph M. Klobucar, Detroit; Frank W. Fenbert, Dearborn, both of Mich.

[73] Assignee: Durr Environmental, Inc., Plymouth, Mich.

[21] Appl. No.: 08/936,877

[22] Filed: Sep. 25, 1997

[51] Int. Cl.[7] .................................................. A61L 2/00
[52] U.S. Cl. .................... 422/2; 422/4; 422/28; 422/33; 422/168; 422/173; 422/175; 422/182; 422/198; 422/206; 422/292
[58] Field of Search .............. 422/2, 4, 28, 33, 422/37, 38, 163, 168, 173, 175, 182, 198, 206, 292

[56] References Cited

U.S. PATENT DOCUMENTS

| | | | |
|---|---|---|---|
| 4,378,334 | 3/1983 | Alguire et al. | 422/182 |
| 5,578,276 | 11/1996 | Klobucar | 422/175 |
| 5,620,668 | 4/1997 | Driscoll et al. | 422/175 |

*Primary Examiner*—Robert Warden
*Assistant Examiner*—Fariborz Moazzam
*Attorney, Agent, or Firm*—Howard & Howard

[57] ABSTRACT

An improved method for processing an industrial sterilization agent utilized to sterilize medical instruments includes the use of a regenerative thermal oxidizer. The sterilization agent is removed from the sterilization chamber and directed into the combustion chamber with little chance for the sterilization agent to mix with air or any other source of oxygen. In this way, the present invention reduces the possibility of explosion of the sterilization agent prior to its being directed into the combustion chamber.

3 Claims, 1 Drawing Sheet

METHOD OF PROCESSING INDUSTRIAL AIR STREAM FOR MEDICAL STERILIZERS

BACKGROUND OF THE INVENTION

This invention relates to a method and apparatus for processing and removing impurities from an industrial air stream utilized to sterilize medical equipment.

In the prior art, various processes have been developed to sterilize medical equipment between each use. One known method includes placing the instruments within a sealed plastic package. The bag has pore sizes that are too small for airborne impurities to enter through the plastic. The bag is placed in a sealed container, and the atmosphere is driven out of the container and replaced with a sterilizing chemical which has the ability to permeate the small pores in the plastic. This sterilizing chemical sterilizes the instrument. The sterilizing chemical is then evacuated from the chamber, and the chamber is then exposed to atmosphere. The instrument will remain sterile until the bag is opened to use the instrument.

These type processes have been very successful in efficiently and effectively sterilizing medical equipment. However, strict regulations require that the sterilizing chemical, typically ethylene oxide, be removed from the industrial air stream before it is returned to atmosphere. In particular, at least 99% of this material must be removed before the industrial air stream can be returned to atmosphere.

It has been the desire of the industry to have the ethylene oxide combusted. In this way, the components of the ethylene oxide are broken down into basic chemical components of carbon dioxide and water. However, ethylene oxide is very volatile. When the ethylene oxide is mixed with even a small amount of oxygen, it can become explosive. Standard oxidizers expose the ethylene oxide to oxygen before the ethylene oxide is directed into a combustion chamber. Thus, prior attempts to combust ethylene oxide are extremely dangerous, and several systems have actually exploded.

The situation has become so grave that regulators have considered reducing the requirement of removing the ethylene oxide, as there has been no safe method proposed to remove the ethylene oxide from the air stream.

In standard chemical manufacturing processes, it has been proposed to remove chemical byproducts and direct them into the combustion chamber of a thermal oxidizer without allowing access to oxygen. These systems have never been proposed for handling ethylene oxide, nor have they been proposed for sterilization systems, or even systems generally in the medical field.

SUMMARY OF THE INVENTION

In a disclosed embodiment of this invention, ethylene oxide is removed from a chamber after it has sterilized medical instruments, and is directed into the combustion chamber of a regenerative thermal oxidizer. At the same time, gas containing little, if any, impurities is directed through the heat exchangers of the regenerative thermal oxidizer and into the combustion chamber. This gas, which is preferably an air stream containing quantities of oxygen, mixes with the ethylene oxide and allows combustion to occur in the combustion chamber.

Preferably, the ethylene oxide is directed into the combustion chamber directly from a sterilization system, with few, and preferably no connections to other pipes which could inadvertently allow leakage of air (and oxygen) into the ethylene oxide flow. Preferably, several sterilization systems are associated with each oxidizer, and yet each sterilization system is piped directly into the combustion chamber. This eliminates the necessity of any connection piping which could be subject to leaking.

The present invention provides a relatively safe way of processing ethylene oxide and removing it from an industrial stream. This system is over 99% efficient in removing the ethylene oxide, and yet removes the danger of explosion of the system.

DETAILED DESCRIPTION OF A PREFERRED EMBODIMENT

Figure 1:
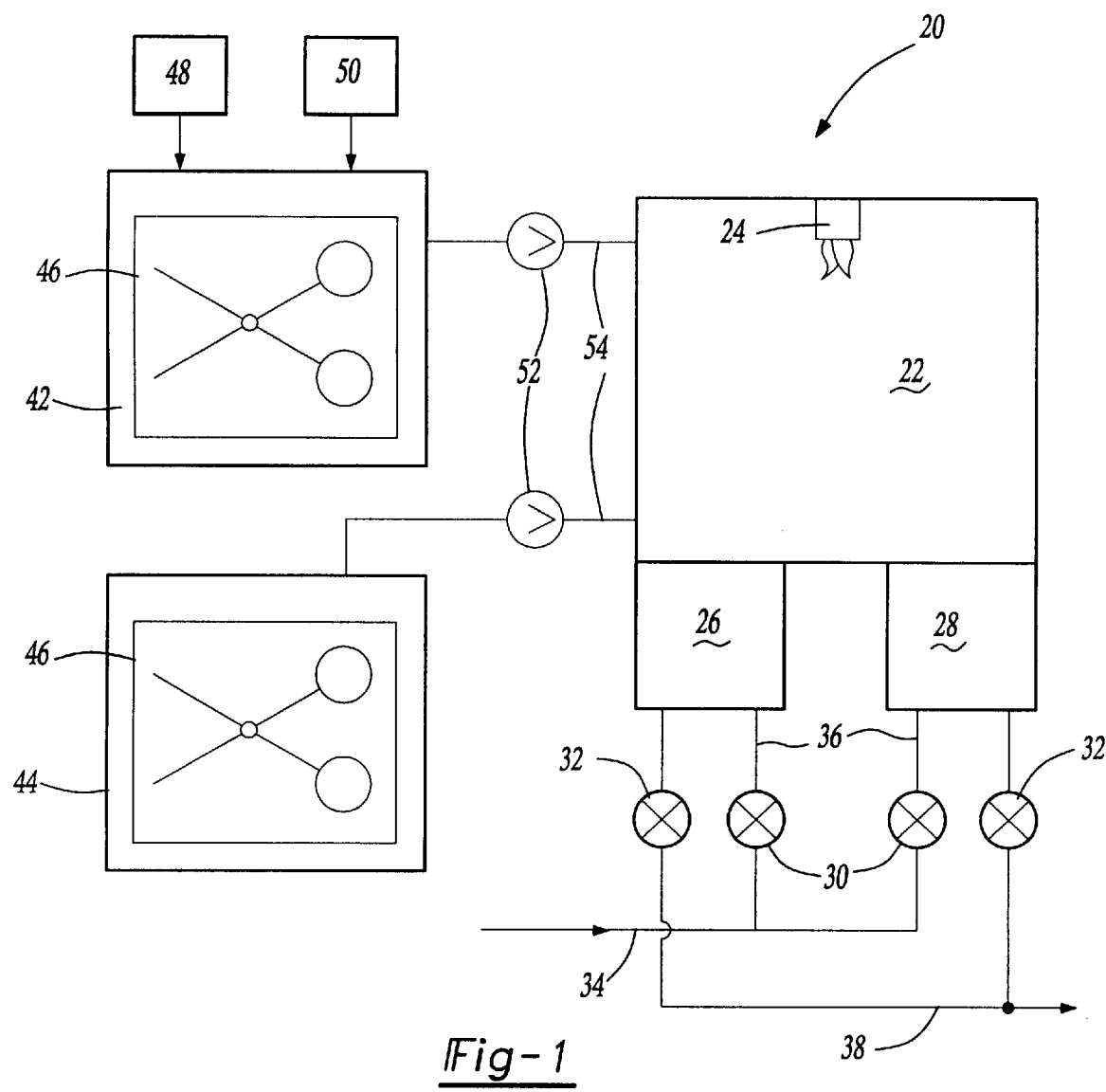
FIG. 1 is a schematic view of a system according to the present invention.

FIG. 1 shows a system 20 somewhat schematically, which includes a regenerative thermal oxidizer having combustion chamber 22 with burner 24. A pair of heat exchangers 26 and 28 receive inlet air through inlet valves 30. Outlet valves 32 control the flow of air out of the heat exchangers 26 and 28. An inlet manifold 34 supplies air through inlet lines 36 and through the valves 30 into the heat exchangers 26 or 28. Similarly, an outlet manifold 38 receives outlet air from the heat exchangers 26 and 28, the lines 40, and valves 32. Although only two heat exchangers are shown, it should be understood that regenerative thermal oxidizers may contain three heat exchangers. Also, although no purge cycle is illustrated, some known regenerative thermal oxidizers include a purge cycle. This invention would extend to regenerative thermal oxidizers that include a purge cycle, and to regenerative thermal oxidizers having a third heat exchanger. As known, regenerative thermal oxidizers serve to process air by passing air in an inlet mode which contains impurities to be removed through a first heat exchanger in an "inlet" mode, and removes the impurities in the combustion chamber. The air from the combustion chamber is continuously moved through a second heat exchanger in an "outlet mode" and to the outlet manifold. The heat exchanger in the inlet and outlet mode cyclically switch. In this way, air is continuously directed into the combustion chamber, is preheated, combusted, and directed toward an outlet manifold where it is cooled by the heat exchanger before being directed to the outlet manifold.

The present invention utilizes a regenerative thermal oxidizer that operates on the same principal. However, the air being directed into the heat exchanger preferably does not include impurities to be removed from the air stream. Instead, the air in the inlet manifold may be atmospheric. The one requirement is that the air stream contain sufficient oxygen to support combustion in a combustion chamber.

The present invention is directed to processing industrial air from sterilization chambers 42 and 44 for medical instruments such as shown at 46. As shown somewhat schematically at 46, the medical instruments are packaged in a plastic package and sealed. The plastic package, typically polyethylene, is preferably of the sort having a pore size that is too small for airborne impurities (micro-organisms) to enter into the plastic package. Thus, once the instrument is sterilized, airborne impurities will no longer be able to contaminate the instrument.

The method of sterilizing is as known in the art. The chamber is evacuated to remove oxygen. Nitrogen from a source 48 is directed into the chamber 42. Once the nitrogen has substantially replaced the oxygen containing air in the chamber 42, a quantity of the sterilizing agent ethylene oxide is directed from source 50 into the chamber 42. Chamber 44 operates in the same manner. Once sterilization is complete, a vacuum pump 52 removes the ethylene oxide from chamber 44 and directs it through a line 54 directly into the combustion chamber 22. Once the ethylene oxide is removed from the chamber 42, the chamber 42 is refilled with atmospheric air.

The present invention relates to the method of directing ethylene oxide from a vacuum pump 52 through a line 54 and directly into the combustion chamber 22. As shown in the drawing, each chamber 42 and 44 has its own pipe 54. This eliminates any connection into the pipe 54 which might allow oxygen to leak into the pipe 54, which could cause an explosion. The air from the inlet lines 36 provides sufficient oxygen to maintain combustion of the ethylene oxide. Preferably, the volumetric flow rate of air directed into the inlet line 36 is at least 20 cubic feet per minute for each one pound per hour of ethylene oxide.

The present invention thus directs the ethylene oxide to a combustion chamber 22 without allowing the ethylene oxide to be exposed to oxygen. In this way, the ethylene oxide cannot combust until it reaches the combustion chamber 22. at the same time, process air is being directed through the heat exchangers 26 and 28 into the combustion chamber 22 to supply oxygen and maintain continuous combustion. In this way, the present invention safely and efficiently removes the ethylene oxide from the industrial air stream.

Figure 2:
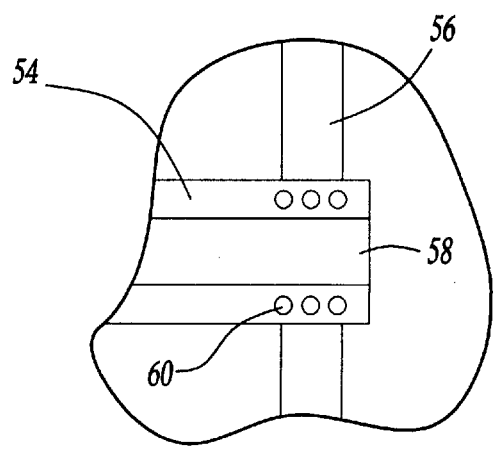
FIG. 2 is a detail of a nozzle for injecting an ethylene oxide gas stream into a combustion chamber.

As shown in FIG. 2, the pipe 54 is preferably provided to be mounted in a wall 56 to the combustion chamber 22 and have a nozzle in 58 with air cooling channels 60. In this way, cooling air can be directed into the nozzle 58 through the channels 60 to cool the nozzle. As known, the heat within the chamber 22 is very high, and the cooling air reduces the likelihood of damage to the nozzle.

While a regenerative thermal oxidizer is disclosed, other type oxidizers such as recuperative oxidizers, direct flow oxidizers, etc., may be used.

While ethylene oxide is disclosed, other potentially explosive sterilizing agents come within the scope of this invention. Preferred embodiments of this invention have been disclosed. However, a worker of ordinary skill in the art would recognize that certain modifications would come within the scope of this invention.

We claim:

1. A method of processing a sterilizing agent comprising the steps of:
    (1) directing a volatile sterilizing agent into a chamber containing a medical instrument;
    (2) sterilizing an instrument within the chamber;
    (3) providing a thermal oxidizer having an air inlet for receiving a source of air and an air outlet for discharging a cleaned outlet air from a combustion chamber;
    (4) removing said volatile sterilizing agent from said chamber and directing said agent into said combustion chamber of said thermal oxidizer, said sterilizing agent mixing with said air to allow combustion of said sterilizing agent in said combustion chamber; and
    said oxidizer is a regenerative thermal oxidizer with heat exchangers that continuously switch from being in an inlet mode to an outlet mode, and said sterilizing agent is directed into said combustion chamber without passing through said heat exchangers.

2. A method as recited in claim 1, wherein said sterilizing agent is ethylene oxide.

3. A method of processing a sterilizing agent comprising the steps of:
    (1) directing a volatile sterilizing agent into a chamber containing a medical instrument;
    (2) sterilizing an instrument within the chamber;
    (3) providing a thermal oxidizer having an air inlet for receiving a source of air and an air outlet for discharging a cleaned outlet air from a combustion chamber;
    (4) removing said volatile sterilizing agent from said chamber and directing said agent into said combustion chamber of said thermal oxidizer, said sterilizing agent mixing with said air to allow combustion of said sterilizing agent in said combustion chamber; and
    (5) there being a plurality of said sterilization chambers, each of said plurality of sterilization chambers being connected directly into said combustion chamber, without first intermixing with each other; and
    (6) wherein said sterilization chambers are connected into said combustion chamber through a cooled nozzle.

* * * * *